United States Patent [19]

van Leemputten

[11] 4,017,364

[45] Apr. 12, 1977

[54] PROCESS FOR PRODUCING AN ENZYME PRODUCT HAVING VARIABLE SOLUBILITY

[75] Inventor: Ekkehard van Leemputten, Clarens, Switzerland

[73] Assignee: Societe d'Assistance Technique pour Produits Nestle S.A., Lausanne, Switzerland

[22] Filed: June 19, 1975

[21] Appl. No.: 588,182

[52] U.S. Cl. .................................. 195/68; 195/63; 195/DIG. 11
[51] Int. Cl.² .......................................... C07G 7/02
[58] Field of Search ............... 195/63, 68, DIG. 11

[56] References Cited

UNITED STATES PATENTS

| | | | |
|---|---|---|---|
| 3,649,457 | 3/1972 | Westman | 195/68 |
| 3,730,841 | 5/1973 | Forgione et al. | 195/63 |
| 3,753,861 | 8/1973 | Forgione | 195/68 |
| 3,847,743 | 11/1974 | Forgione | 195/63 |

*Primary Examiner*—Lionel M. Shapiro
*Attorney, Agent, or Firm*—Kenyon & Kenyon Reilly Carr & Chapin

[57] ABSTRACT

An enzymatically active product is prepared by reacting an enzyme, e.g. trypsin, with a polymer carrying both free aldehyde groups and free acid groups, e.g. a copolymer of acroelin and acrylic acid containing at least 10 % of free aldehyde groups based on the total of free aldehyde and acid groups. The product has a variable solubility in aqueous medium so that the enzyme bound to the polymer can be recovered for reuse by adjusting the pH to precipitate the polymer.

11 Claims, No Drawings

PROCESS FOR PRODUCING AN ENZYME PRODUCT HAVING VARIABLE SOLUBILITY

BACKGROUND OF THE INVENTION

This invention relates to a process for the preparation of an enzymatically active product.

Enzymatic reactions are normally carried out with one or more enzymes in solution in the medium containing the substance which it is desired to subject to the action of the enzyme and which is known as the substrate. Thus dissolved in the reaction medium, the enzyme can only be separated from the substrate with extreme difficulty and generally the enzyme has to be inactivated, for example by heating, in order to stop the reaction. Accordingly, this enzyme is not reusable.

Numerous processes for the preparation of enzymatically active products insoluble in aqueous medium have been proposed with a view to obviating these disadvantages. The enzymatic reactions carried out with these products may be conducted either by percolation of the substrate through a column filled with insoluble product or by dispersion of the product in the solution containing the substrate and by mechanical separation of the insoluble product. In every case, the insoluble, enzymatically active product is readily recoverable and, at least in theory, indefinitely reusable.

However, there are serious limitations to the use of these insoluble enzymatically active products, because the successful execution of a chemical, i.e. enzymatic, reaction requires that a certain number of conditions be satisfied.

The first requirement, which is imperative, is that the reactants should be able readily to contact one another, i.e. in the present case that the substrate should have fairly free access to the insoluble enzymatically active product and, more especially, to the active site. Accordingly, it is essential that there should be, at one and the same time, a high level of physico-chemical affinity between the two reactants present, reduced steric congestion around the active site and, concurrently or correlatively, a certain flexibility of the enzymatically active product. Although this first requirement of "good contact" might be satisfied, the enzyme-substrate exchange rate also has to be suitable and must ensure the rapid departure of one molecule of substrate which has reacted and its immediate replacement by a molecule which has not yet reacted.

The conditions under which the reaction between the substrate and the insoluble enzymatically active product is carried out are generally unfavourable. Accessibility and exchange rate are poor as a result of the heterogeneity of the reaction medium (solid-liquid), the poor accessibility being aggravated by the fact that the product is a solid polymer and, hence, shows a pronounced degree of rigidity. In addition, this polymer frequently comprises a hydrocarbon-containing skeleton which shows little affinity on the one hand for the aqueous phase (poor wettability) and on the other hand for the substrates which are generally polar.

Accordingly, the insoluble products normally have a low enzymatic activity by comparison with the corresponding free enzyme and, hence, give mediocre reaction yields. An object of the invention is to eliminate these limitations.

THE INVENTION

The present invention provides a process for the preparation of an enzymatically active product which comprises reacting an enzyme with a polymer carrying both free aldehyde and free acid groups.

The invention also relates to the product obtained by the process defined above which is characterised by its variable solubility in aqueous medium. This product combines the advantages of the corresponding free enzymes, i.e. accomplishment of the enzymatic reaction in homogeneous liquid medium, with the advantages of "insolubilised enzymes" because it is possible, by adjusting the pH, to recover the product on completion of the reaction by a simple mechanical separation and then reuse it.

DISCUSSION OF THE INVENTION AND ITS PREFERRED EMBODIMENTS

In the context of the invention, free aldehyde groups are aldehyde groups which are carried by the polymer and which are available to enter into chemical bonds with other substances. Similarly, free acid groups are acid groups which are carried by the polymer and which are capable of being ionised to impart to the enzymatically active product a high level of solubility and of being returned to their non-ionic form by reasonable reduction of the pH, thereby drastically restricting the solubility of the product. Acid groups of this type are, for example, carboxylic acid groups and phenol groups.

A polymer containing free aldehyde and acid groups may be obtained by the polymerisation of a suitable monomer or by the copolymerisation of, for example, a mixture containing a monomer giving the free aldehyde groups and a monomer giving the free acid groups, or even by the creation of free aldehyde groups and/or free acid groups on a suitable polymer. It is essential to provide for the presence of a sufficient number of free acid groups to ensure the variable solubility required. It has been found that the presence of approximately 5 % of free acid groups among all the free aldehyde and acid groups provides for this variable solubility. Obviously a minimum number of free aldehyde groups is required for arresting the enzyme. There is no practical interest in ascertaining a value for this minimum quantity, because it is desirable to have as many free aldehyde groups as possible to be able to fix as much enzyme as possible and hence to obtain, after fixation, a product with interesting enzymatic activity. Experimental determination of the presence of these free aldehyde groups, and their dosage, may be carried out on the polymer in precipitatedform by Park and Johnson's method adapted to the insoluble materials, as described by J. S. Thompson and G. D. Schockman in Anal Biochem. 22, 260 (1968).

The process according to the invention is applicable to enzymes which contain functional groups capable of reacting with the free aldehyde groups by an irreversible reaction. Examples of these functional groups include the free amino groups carried by certain amino acids, such as lysine.

It has been found that the various parameters referred to above do not have any critical effect upon the process by which the enzyme is fixed to the polymer. Providing the characteristics of the medium do not affect the nature of the enzyme and the polymer, they do not have any significant influence upon the fixation process. It is necessary, for example, to avoid the presence in the medium of alkaline earth metal ions which have a tendency to react with the polymer in acid medium, thus preventing its subsequent redissolution. There are no crucial limits to the quantities and concentrations of enzyme and polymer to be used. The pH does not play any significant part either, fixation taking place equally satisfactory on a polymer in solution or on a solid, adequately divided polymer. Generally, any pH-value between 1 and 11, providing it does not affect the integrity of the enzyme and the polymer, is suitable, although the fixing reaction is preferably carried out at a pH-value of from 7 to 8 at which the polymer is in solution. Similarly, although the fixing reaction is preferably carried out at ambient temperature, it may also be carried out at a higher temperature, but of course below the temperature at which the enzyme is inactivated.

Finally, the reaction times may vary from a few minutes to several hours. However, the best results have been obtained with reaction times of from 1 to 3 hours.

In cases where fixation of the enzyme has been carried out in heterogeneous medium on a polymer in solid form, recovery of the enzymatically active product is particularly simple and may be carried out by any mechanical separation means, such as filtration, decantation, centrifuging, etc. In the opposite case, it is sufficient to acidify the medium to a pH-value generally of the order of 4.5, if the free acid groups are all carboxylic acid groups, to precipitate the enzymatically active product which may then be recovered in the same way as described above.

The product obtained has a variable solubility which, as already mentioned, is governed by the pH. It is pointed out that, in cases where the free acid groups are all carboxylic acid groups, the precipitation pH is also 4.5 which signifies that the presence of enzyme fixed to the polymer does not appreciably alter the solubility characteristics thereof. Thus, at a high pH, the enzymatically active product will be soluble and will be extremely similar in its behaviour to the free enzyme. By contrast, at a low pH, the product will precipitate and may readily be separated. After washing, this product may be reused in another cycle comprising dissolution followed by reprecipitation, and so on. Obviously care will have been taken in selecting, as the enzyme to be fixed to the polymer, an enzyme which develops its maximum activity or a substantial level of activity in a pH zone where the enzymatically active product obtained after fixation is soluble in aqueous medium. It is advisable to point out that the maximum activity of the free enzyme is not necessarily developed at the same pH as the maximum activity of the "product of fixation", because the abundance of negative charges in this product, produced by ionisation of the acid groups carried by the polymer, creates an accumulation of protons in the immediate environment of the fixed enzyme. There are as many protons which will not have been supplied by the reaction medium during the enzymatic reaction and, in overall terms, a maximum activity situated at a slightly more basic pH may be measured for the enzymatically active product than for the corresponding free enzyme.

In one particular embodiment of the process according to the invention, an enzymatically active product with variable solubility in aqueous medium is prepared by reacting an enzyme with a copolymer of acrolein and acrylic acid containing at least 10 % of free aldehyde groups. This copolymer may be formed by various polymerisation mechanisms, including radical polymerisation, which is initiated by redox systems, anionic polymerisation and cationic polymerisation. This copolymer, which may be prepared in aqueous medium or in an organic solvent, has a structure which is governed both by the respective quantities of the two monomers in the starting mixture and by the polymerisation process used.

Fixation of the enzyme to the copolymer is with advantage carried out in a buffer solution by mixing the enzyme and the copolymer with vigorous stirring for 1 to 3 hours at ambient temperature. The reaction is preferably carried out in aqueous homogeneous phase using a buffer of pH 8 over a period of 1 hour, at the end of which the pH is lowered to 4 and the precipitate formed is collected by filtration. The enzyme part of the product is thus bound to the polymer part by a condensation group between an aldehyde groups and the enzyme.

In this particular embodiment, it is possible for example to prepare a fixation product of the aforementioned copolymer and trypsin which has 50 to 80 % of the enzymatic activity of free trypsin and which is soluble in aqueous medium at a pH-value above about 4.5 and insoluble at a pH below that value.

EXAMPLES

The process according to the invention is illustrated by the following Examples.

EXAMPLE 1 a. Preparation of the acrolein/acrylic acid copolymer

A mixture containing 450 ml of degassed oxygen-free water, 60 ml of freshly distilled acrolein, 9 ml of acrylic acid, 6.6 ml of a solution of water oxygenated to 30 % and 12 ml of 2 N sulphuric acid, is prepared in a nitrogen atmosphere. 150 ml of a 2.75 % solution of sodium nitrite in degassed water is then progressively added over a period of about 40 minutes. On completion of the reaction, the pH-value is between 3 and 4 and the copolymer is present in precipitated form. After filtration, the precipitate is washed first with a solution of 0.002 M hydrochloric acid and then with acetone and dried. 7.75 g of the required copolymer are thus obtained. The presence of free aldehyde groups is detected by measuring the reducing power by the method J. S. Thompson et al already referred to in the text. In addition, the presence of free acid groups is detected by titration. It is found that 14 % by weight of the copolymer is in the form of free aldehyde groups and 17.6 % in the form of free acid groups.

b. Fixation of trypsin to the copolymer 600 mg of the copolymer prepared in accordance with a. are dissolved at ambient temperature in 150 ml of a 0.2 M phosphate buffer with a pH-value of 8. During dissolution and also subsequently during the fixation reaction, this pH-value is kept at 8 by the addition of a 1 N soda solution. After complete dissolution of the polymer, 150 mg of crystallised trypsin are added and the mixture left to react for 1 hour at ambient temperature. The pH-value is then lowered to 4 by the addition of hydrochloric acid. The precipitate formed is filtered and washed 3 times with water. 557 mg of enzymatically active product are obtained after drying.

c. Determination of the enzymatic activity of the product

The method used is an adaptation to the determination of trypsin of the method of S. Blomberg et al described in Eur. J. Biochem 15, 97 (1970).

A 0.009 M solution of BAEE (α,N-benzoyl-L-arginine ethyl ester hydrochloride) is prepared by dissolving 306 mg of this substrate in 100 ml of a 0.016 M $Ca^{++}$ (in the form of $CaCl_2$) and 0.3 M KCl solution.

3 μg of trypsin (in the form of a solution) are added to 5 ml of this solution and the quantity of carboxylic acid groups liberated by enzymatic hydrolysis at the level of the ester function of the BAEE is measured as a function of time. Measurement is carried out by automatic titration with 0.01 M soda solution using the so-called "pH-stat" manufactured by Methrohm Herisau, with graphic recording of the quantity of soda solution consumed in keeping the pH at its value of 8. The curve thus obtained has a long straight section of which the slope represents the consumption of soda per unit of time. This same test is repeated with 5 μg, 7.75 μg, 10 μg and, finally, 13 μg of trypsin. A calibration curve is then drawn, representing the consumption of soda per unit of time/quantity of trypsin. This curve is a straight line. In other words, the consumption of soda is proportional to the quantity of trypsin used.

Finally, this test is repeated using 12 μg of enzymatically active product (in the form of a solution: pH 8). By direct reading, the consumption of soda, as shown by the calibration curve, gives the equivalent quantity of trypsin, i.e. taking into account the quantity of trypsin fixed to the polymer, an enzymatic activity of 80 %.

d. Solubilities of the product 93 mg of enzymatically active product, prepared in accordance with (b), are dissolved in 25 ml of a solution of a 0.2 M phosphate buffer of pH 8. The enzymatic activity of the solution is measured by the method described in (c) which is given the coefficient 100. 1 N hydrochloric acid is progressively added; the product precipitates gradually.

Samples are taken at regular intervals and centrifuged. The residual enzymatic activity of the supernatant phase is then measured. It is found that the enzymatic activity of the liquid suddenly decreases around a pH of 8.4. The value measured at pH 6 is still 98 %, whereas at pH 4.6 it has fallen to 2 %. The residual activity is zero below pH 4.5. In other words, all the enzymatically active product has been converted into insoluble form. The insoluble product thus obtained is redissolved in a solution of pH 8 and the enzymatic activity of the solution is determined. It is found to have 98 % of the enzymatic activity of the starting solution.

This enzymatically active product may thus be quantitatively separated from the enzymatic reaction medium by lowering the pH to a value below 4.5 and may be reused without significant losses by redissolution at a pH-value of around 8 at which trypsin develops its maximum enzymatic activity.

EXAMPLE 2

200 mg of the acrolein/acrylic acid copolymer prepared in accordance with Example 1, 50 mg of crystallised trypsin and 50 ml of a 0.05 M TRIS buffer of pH 8 (dissodium ethylenediamine tetraacetate) are mixed together. The mixture is left standing for 24 hours at a temperature of 4° C, after which the pH is lowered to 4 by the addition of hydrochloric acid. The precipitate formed is filtered and washed 3 times with water. After drying, an enzymatically active product is obtained with the same characteristics as the product prepared in accordance with Example 1.

I claim:

1. A process for the preparation of an enzymatically active product having a variable solubility in an aqueous medium dependent on pH, comprising reacting an enzyme with a polymer carrying both free aldehyde groups and free acid groups, said free acid groups being present in a sufficient number to ensure the variable solubility of the product.

2. A process according to claim 1, in which said polymer contains at least 5 % of free acid groups based on the total of free aldehyde and acid groups.

3. A process according to claim 1 in which said polymer is a copolymer of acrolein and acrylic acid containing at least 10 % of free aldehyde groups based on the total of free aldehyde and acid groups.

4. A process according to claim 2 wherein said enzyme is trypsin.

5. A process according to claim 3, in which said enzyme is trypsin.

6. A process according to claim 1, in which said enzyme is reacted with said polymer by mixing said two substances in a buffer solution to produce a product which is precipitated and collected by filtration.

7. A process according to claim 6, in which said buffer solution has a pH-value of 7 to 8.

8. A process according to claim 7, in which said enzyme is trypsin.

9. A process for the production of an enzymatically active product having a variable solubility in aqueous medium comprising reacting an enzyme with a copolymer of acrolein and acrylic containing at least 10 % of free aldehyde groups, based on the total of free aldehyde and acid groups, by mixing said enzyme and said copolymer in a buffer solution with vigorous stirring for 1 to 3 hours at ambient temperature to produce a product which is precipitated and collected by filtration.

10. A process according to claim 9 in which said reaction is carried out in aqueous homogeneous phase using a buffer of about pH 8 for about 1 hour after which said pH is lowered to about 4 to precipitate said product.

11. A process according to claim 10 in which said enzyme is trypsin.

* * * * *

UNITED STATES PATENT AND TRADEMARK OFFICE
CERTIFICATE OF CORRECTION

PATENT NO. : 4,017,364
DATED : April 12, 1977
INVENTOR(S) : Ekkehard VanLeemputten It is certified that error appears in the above-identified patent and that said Letters Patent are hereby corrected as shown below:

Column 2, line 53, change "precipitatedform to --precipitated form--.

Column 4, line 19, change "groups" to --group--.

Column 4, line 48, after "method" insert --of--.

Signed and Sealed this fifth Day of July 1977

[SEAL]

Attest:

RUTH C. MASON
*Attesting Officer*

C. MARSHALL DANN
*Commissioner of Patents and Trademarks*